United States Patent [19]

Parel et al.

[11] Patent Number: 5,281,211
[45] Date of Patent: * Jan. 25, 1994

[54] NONCONTACT LASER MICROSURGICAL APPARATUS

[75] Inventors: Jean-Marie Parel, Miami Shores, Fla.; Takashi Yokokura, Tokyo; Katsuhiko Kobayashi, Chiba, both of Japan

[73] Assignee: University of Miami, School of Medicine, Dept. of Ophthalmology, Miami, Fla.

[*] Notice: The portion of the term of this patent subsequent to Oct. 6, 2009 has been disclaimed.

[21] Appl. No.: 788,513

[22] Filed: Nov. 6, 1991

Related U.S. Application Data

[62] Division of Ser. No. 363,174, Jun. 7, 1989, Pat. No. 5,152,759.

[51] Int. Cl.[5] ............................................. A61N 5/02
[52] U.S. Cl. ........................................... 606/5; 606/4; 606/13; 606/17; 606/2
[58] Field of Search ......................................... 606/2–19; 124/395, 397, 398

[56] References Cited

U.S. PATENT DOCUMENTS 4,729,372 3/1988 L'Esperance, Jr. ..................... 606/5
4,887,592 12/1989 Loertscher ............................. 606/5
5,152,759 10/1992 Parel et al. ............................ 606/17

FOREIGN PATENT DOCUMENTS

3535073 4/1987 Fed. Rep. of Germany .......... 606/5

*Primary Examiner*—David M. Shay
*Attorney, Agent, or Firm*—Finnegan, Henderson, Farabow, Garrett & Dunner

[57] ABSTRACT

A noncontact laser microsurgical apparatus and method for marking a cornea of a patient's or donor's eye in transplanting surgery or keratoplasty, and in incising or excising the corneal tissue in keratotomy, and for tissue welding and for thermokeratoplasty. The noncontact laser microsurgical apparatus comprises a laser source and a projection optical system for converting laser beams emitted from the laser source into coaxially distributed beam spots on the cornea. The apparatus further includes a multiple-facet prismatic axicon lens system movably mounted for varying the distribution of the beam spots on the cornea. In a further embodiment of the method of the present invention, an adjustable mask pattern is inserted in the optical path of the laser source to selectively block certain portions of the laser beams to thereby impinge only selected areas of the cornea.

18 Claims, 7 Drawing Sheets

NONCONTACT LASER MICROSURGICAL APPARATUS

This is a divisional of Ser. No. 07/363,174 now filed Jun. 7, 1989, now U.S. Pat. No. 5,152,759.

BACKGROUND OF THE INVENTION

1. Field of the Invention

The present invention relates to a microsurgical apparatus and, more particularly, a noncontact laser microsurgical apparatus adapted for use in cornea transplant surgery, keratoplasty, keratotomy, and other corneal surgery techniques.

2. Description of the Related Art

Despite advances in corneal preservation and transplantation techniques, postoperative astigmatism remains the most important complication limiting visual acuity after a corneal transplantation.

In order to reduce such postoperative astigmatism, U.S. patent application Ser. No. 07/056,711 filed Jun. 2, 1987 entitled "A Cornea Laser-Cutting Apparatus", assigned to the same assignee as the present application, discloses that trephination of either a donor cornea or a recipient cornea may be performed utilizing a laser cutting technique.

During penetrating keratoplasty, it is further necessary for a surgeon to align the circumferences of the donor corneal button and recipient cornea. To this end, there have been recently developed mechanical marking apparatuses such as those described in Pflugfelder et al. "A Suction Trephine Block for Marking Donor Corneal buttons," Arch. Ophthalmol., Vol. 106, Feb. 1988, and Gilbard et al. "A New Donor Cornea Marker and Punch for Penetrating Keratoplasty," Ophthalmic Surgery, Vol. 18, No. 12, Dec. 1987.

However, such mechanical marking apparatuses directly contact and distort the cornea such that the marking process is not always precisely accomplished and sometimes results in post-keratoplasty astigmatism.

In radial keratotomy, mechanical contact type surgical utensils as shown in U.S. Pat. No. 4,417,579 have been used to radially incise the cornea of a patient's eye. This surgical method is apt to cause strain and/or deformation of the cornea, and also results in postoperative astigmatism.

Noncontact microsurgery of the cornea would minimize distortion of the cornea tissue, as occurs in contact-type techniques, and would decrease the likelihood of producing postoperative astigmatism. The use of lasers provides the potential for such noncontact microsurgery.

Excimer lasers have been investigated in the past to produce linear corneal incisions or excisions. The argon fluoride excimer laser emitting at 193 nm has been shown to produce sharp, smooth-walled corneal cuts. More recently, the hydrogen fluoride, Q-switched Er:YAG, and Raman-shifted Nd:YAG lasers emitting at about 2.9 um (micro meters), which corresponds to the peak absorption wavelength of water, have been experimentally used to produce linear corneal incisions or excisions.

Industrial laser cutting by focusing the beam into a ring has been proposed as a method for drilling large diameter holes. The axicon, a diverging prismatic lens, has been used for such industrial purposes. An axicon system has been used by Beckman & Associates to study corneal trephination with a carbon dioxide laser. This experimentation is described in an article entitled "Limbectomies, Keratectomies and Kerastomies Performed With a Rapid-Pulsed Carbon Dioxide Laser," American Journal of Ophthalmology, Vol. 71, No. 6, (Jun. 1971). In this article, Beckman et al. describe the use of an axicon lens in combination with a focusing lens to form an "optical trephine" and perform various corneal experiments with animal's. The diameter of the trephine was governed by the focal length of the focusing lens in these experiments. Therefore, to vary the diameter of the annular beam it was necessary to change the focusing lens which acted to change the width of the annular ring and, thus, varied the amount of tissue incised or excised by the laser. Moreover, changing the focusing lens requires a time consuming process for each patient or donor. In addition, the optical system proposed in the Beckman et al. article requires the use of multiple focusing lenses of different focal length.

Accordingly, it is an object of the present invention to provide a noncontact laser microsurgical apparatus and method of using the same which substantially eliminates strain and/or deformation on a cornea during and after trephination.

Yet another object of the present invention is to provide a noncontact laser microsurgical apparatus and surgical method which is capable of marking a recipient cornea and a donor corneal button with a suture track during keratoplasty, and which incises or excises selected portions of a cornea radially and/or paraxially during keratotomy.

Still another object of the present invention is to provide a noncontact laser microsurgical apparatus and surgical method which is capable of performing thermokeratoplasty for curing corneal refractive error and/or astigmatism of a patient's eye.

It is still another object of the present invention to provide a noncontact laser microsurgical apparatus and method capable of surgically "welding" donor tissue or synthetic material and recipient corneal tissue together thereby eliminating the necessity of suturing the donor and recipient parts to one another in penetrating and epikeratoplasty procedures.

It is still a further object of the present invention to provide a noncontact laser microsurgical apparatus and method wherein selected areas of the cornea may be caused to shrink so as to change the curvature of the natural lens thereby curing or alleviating corneal refractive error and/or asigmatism.

Additional objects and advantages of the invention will be set forth in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

To achieve the foregoing objects, and in accordance with the purposes of the invention as embodied and broadly described herein, the noncontact laser microsurgical apparatus of the present invention comprises means for generating laser beams; and means for projecting the laser beams onto a cornea. The projection means defines an optical axis and includes means for converging the laser beams. The projecting means further includes axicon optical means for forming the projected beams into a plurality of paraxially distributed spots on the cornea, and means for varying the radial position of the spots.

Preferably, the converging means includes a focusing lens and the axicon optical means includes at least one multiple-facet prismatic ("MFP") axicon lens mounted for movement along the optical axis of the projecting means.

The generating means may comprise an infrared pulse laser beam generator with a preferred wavelength of about 1.3-3.3 um. Also, an ultra-violet laser source may be used such as an Argon fluoride laser emitting at 193 nm.

The projecting means preferably includes beam expander means for enlarging the radius of the laser beam emerging from the generating means.

The apparatus may also include aiming means for projecting visible laser beams onto the cornea substantially coincident with the positions at which the laser beams projected through the axicon means impinge the cornea. The optical axis of the aiming means preferably overlaps with at least a portion of the optical axis of the projecting means. Preferably, the aiming means includes a visible laser beam source, and a mirror obliquely interposed between the beam expander means and the converging means for reflecting the visible laser beams and allowing the laser beams from the generating means to pass therethrough.

The apparatus of the present invention may also include mask means disposed in the optical axis for selectively blocking portions of the projected laser beams while transmitting the remaining portions of the projected laser beams therethrough. In this manner incisions or excisions in the corneal tissue may be made only in selected areas of the cornea corresponding to the transmitting portions of the mask means.

The present invention also provides a microsurgical method for ablating the cornea in selected areas by appropriate use of the disclosed apparatus. Moreover, by careful selection of the laser generating means the corneal tissue may be heated only sufficiently to cause shrinkage of the tissue in selected areas to alleviate astigmatism and/or corneal refractive error. Furthermore, by appropriate control of the selected laser generating means donor and recipient corneal tissue may be heated in abutting areas to cause the disparate tissue to adhere to one another in the manner of a surgical weld to thereby eliminate the need for sutures.

BRIEF DESCRIPTION OF THE DRAWINGS

The accompanying drawings, which are incorporated in and constitute a part of the specification, illustrate presently preferred embodiments and methods of the invention and, together with the general description given above and the detailed description of the preferred embodiments and method given below, serve to explain the principles of the invention. In the drawings.

DESCRIPTION OF THE PREFERRED EMBODIMENTS AND METHOD

Reference will now be made in detail to the presently preferred embodiments and method of the invention as illustrated in the accompanying drawings in which like reference characters designate like or corresponding parts throughout the several drawings.

An optical delivery system of a noncontact laser microsurgical apparatus incorporating the teachings of the present invention includes means for generating laser beams.

Figure 1:
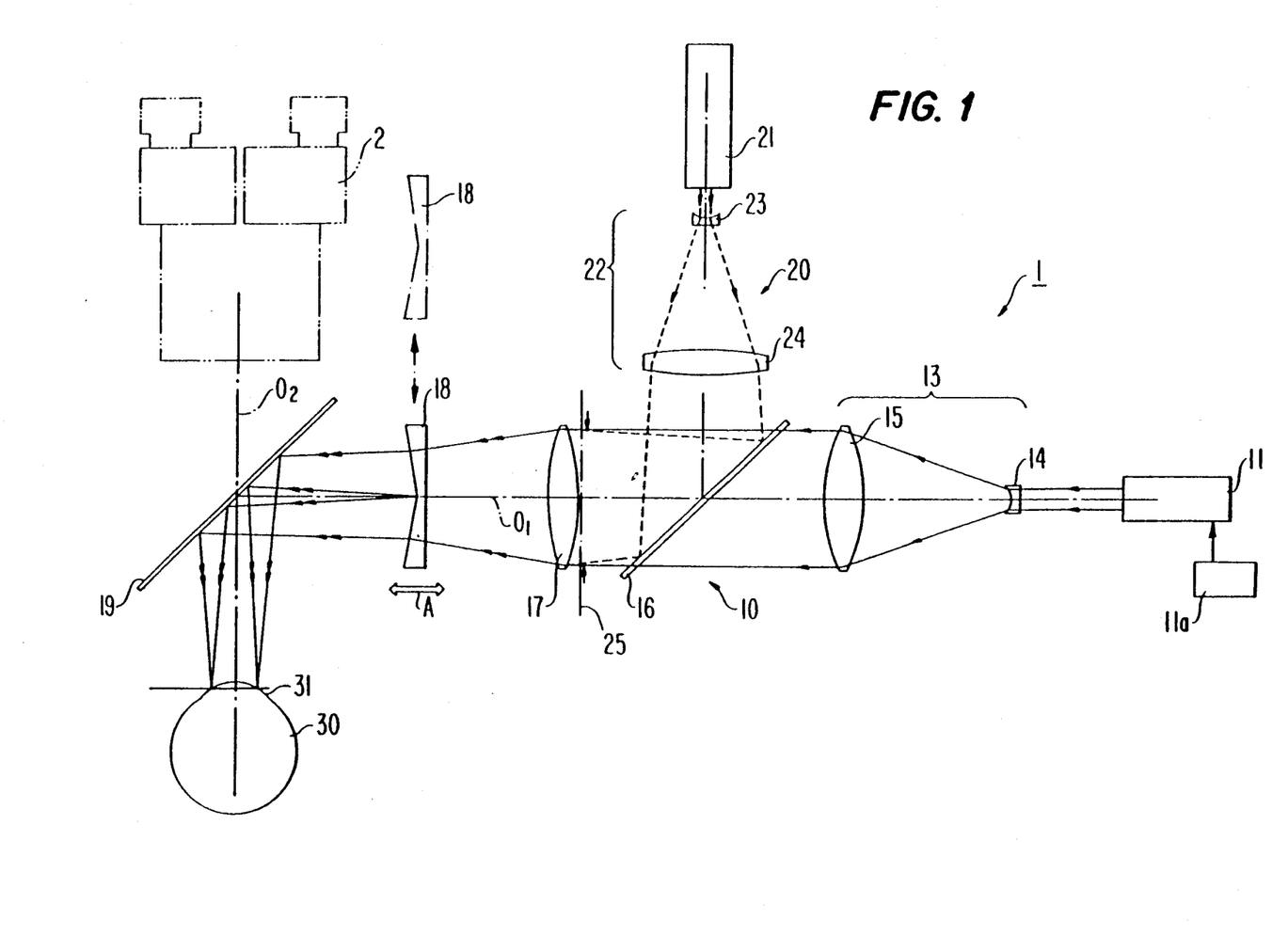
FIG. 1 illustrates an optical system arrangement of a non-contact laser microsurgical apparatus incorporating the teachings of the present invention.

As illustrated in FIG. 1 and embodied herein, the generating means of apparatus 10 comprises a laser source 11 which generates pulsed laser beams that are capable of ablating the tissue of a living organ, i.e., a cornea. Lasers which meet the requirements described above may include HF (Hydrogen Fluoride) lasers and Er-YAG (Erbium-Yttrium Aluminum Garnet) lasers which emit infrared pulses having wavelengths of about 2.0 to about 3.0 um, and preferably about 2.9 um, and which have a pulse duration of less than 200 ns and an energy flux of greater than about 250 mj/cm². Also operable with the present invention are ArF (Argon Fluoride) lasers which produce an ultra-violet laser beam having wavelengths of less than about 200 nm with a pulse duration of about 10–23 ns and an energy flux of about 70 mj/cm². Laser source 11 is connected to a radiation control switch 11a. When the control switch is moved to the "on" position laser source 11 generates infrared pulsed beams. Radiation control switch 11a is preferably capable of controlling the energy of the pulse beams by insertion of a neutral density filter (not shown) in a transmitting path thereof.

In instances where it is desirable to heat the corneal tissue without causing ablation, the laser source selected may be an C.W.HF, or Holmium, or Nd:YAG laser emitting at a wavelength of 1.3–3.3 um, a pulse duration of greater than 200 n sec, and an energy flux of about 250 mJ/cm².

In accordance with the present invention, the apparatus includes means for projecting the laser beams along an optical axis onto the cornea. As embodied herein, the projecting means includes a beam expander means, generally referred to as 13, for expanding the laser beam generated by laser source 11. Beam expander means 13 includes a concave lens 14 and a convex lens 15. Laser beams emerging from convex lens 15 are formed in parallel and are in turn projected along optical axis $O_1$. The beam expander means may also comprise a variable diverging beam expander comprised of a conventional zooming optical system or a pair of movable convex-concave axicon lenses described in the above-mentioned U.S. patent application Ser. No. 056,711.

In accordance with the present invention, the apparatus includes means for converging the projected laser beams onto the cornea. As embodied herein, the converging means includes a condensing and focusing lens 17 which functions to condense and focus light passing therethrough onto a focal plane. The position of the focal plane is determined in accordance with the geometry of the lens as will be well understood by those skilled in the art. Beam expander 13 also acts to increase the laser beam diameter entering lens 17, thereby increasing the numerical aperture of the optical system. Consequently, the focal spot of the beam at the focal plane of lens 17 is reduced.

In accordance with a first embodiment of the present invention, the apparatus includes axicon optical means for forming the converged laser beams into a plurality of paraxially distributed beam spots on the cornea. As embodied herein the axicon optical means may comprise a multiple-facet prismatic ("MFP") lens 18.

Figure 2A:
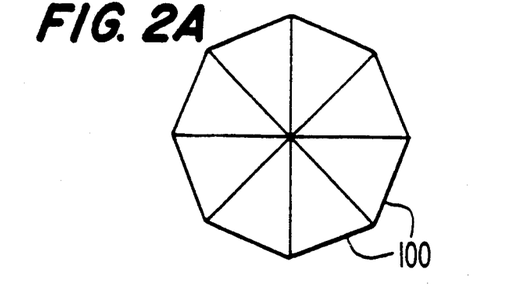
FIG. 2A is a plan view of a concave MFP axicon lens.
Figure 2B:
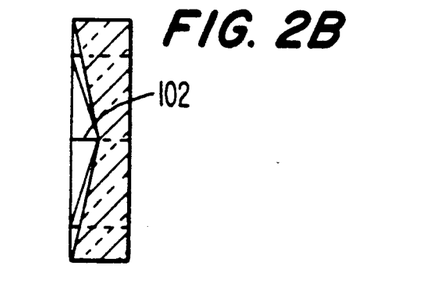
FIG. 2B is a cross-sectional view of the MFP axicon lens shown in FIG. 2A.
Figure 3A:
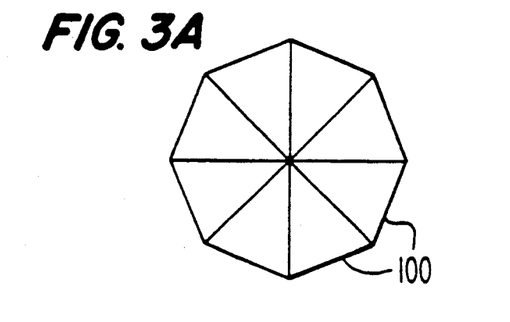
FIG. 3A is a plan view of a convex MFP axicon lens.
Figure 3B:
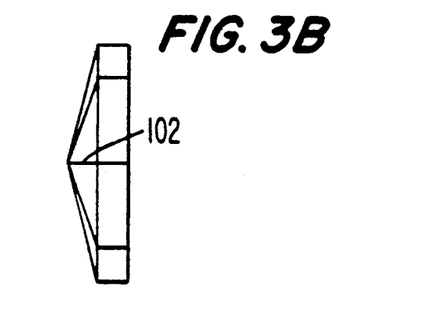
FIG. 3B is a side view of the MFP axicon lens shown in FIG. 3A.
Figure 6:
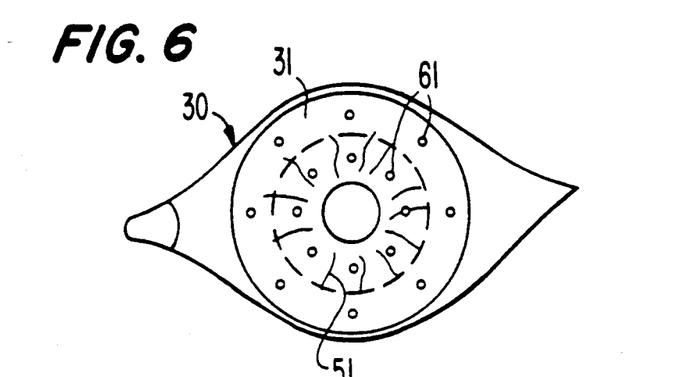
FIG. 6 is a plan view of an alignment of a donor corneal button with a recipient cornea with spot marks defining a suture track in each.

As shown in FIGS. 2A and 2B, axicon lens 18 may be configured with concave multiple-facet prisms (eight-facet prisms, for example) whose outer edges (prism bases) 100 are larger in width than the optical axis portion 102 thereof. Axicon lens 18 may also be configured with convex multiple-facet prismatic lenses as shown in FIGS. 3A and 3B whose outer edges (prism bases) 100 are larger in width than optical axis portions 102 thereof. With reference to FIG. 6, the multiple-facet prism function of axicon lens 18 causes the converging laser beams emerging from lens 18 to be formed into a plurality of paraxially distributed beam spots 61 on cornea 31 of eye 30. The spots 61 are radially spaced from the apex of cornea 31 and from optical axis $O_1$. Preferably, the laser beams are converged onto cornea 31 of eye 30 (a patient's eye or donor's eye or tissue held in the holding device shown in FIG. 4) after reflection by a dichroic, mirror 19 as shown in FIG. 1. As a result, cornea 31 is marked, excised, or incised by the laser beam energy at spots 61.

It is necessary to vary the cornea marking, excising, or incising diameters in keratoplasty and keratotomy. To this end, the present invention may include means for moving the axicon optical means along the optical axis $O_1$. Furthermore, in order to carry out curved keratotomy in accordance with the present invention, means may be provided to rotate the axicon optical means about the optical axis. Furthermore, to perform radial keratotomy, means may be provided for moving the converging means along the optical axis.

As embodied herein, movement of the axicon optical means comprised of MFP lens 18, and movement of the converging means comprised of focusing lens 17 along optical axis $O_1$, and rotation of MFP axicon lens 18 about optical axis 01, may be carried out by a known electro-mechanical device (not shown) which may comprise a combination of stepping motors, for example, controlled by a microprocessor or minicomputer (not shown). By way of example and not limitation, model no. SPH-35AB-006 stepping motors manufactured by Tokyo Electronic Co., Ltd. may be used to move MFP lens 18 and focusing lens 17.

In accordance with the present invention, the microsurgical apparatus incorporating the teachings of the present invention may include aiming means for projecting visible light beams onto the cornea substantially coincident with the positions at which the laser beams are to impinge the cornea. As embodied herein, the aiming means comprises an aiming system 20 which includes a He-Ne laser source 21 for generating visible light beams, beam expander means 22, and dichrotic beam combiner 16. Beam expander means 22 may comprise a concave lens 23 and a convex lens 24. Dichrotic beam combiner 16 is positioned in optical axis $O_1$ and is selected such that it functions to reflect incident He-Ne laser beams, while laser beams from source 11 pass therethrough.

He-Ne laser beams from laser source 21 are enlarged in diameter by expander means 22, whose output laser beams, in turn, are projected onto condensing and focusing lens 17 after reflection by cold mirror 16. Thus, laser beams from source 21, which are reflected by mirror 16, are coincident with a portion of optical axis $O_1$.

For observing the cornea and the He-Ne laser beams projected thereon, the noncontact laser microsurgical apparatus may also include viewing means comprised of an operation microscope 2, indicated by phantom lines in FIG. 1. The configuration and function of operation microscopes is well known in the ophthalmology field, therefore, its detailed description is omitted. By way of example and not limitation, a model no. OMS-600 microscope manufactured by TOPCON CORPORATION may be used.

An optical axis $O_2$ of operation microscope 2 is disposed to be coincident with a portion of optical axis $O_1$ of the noncontact laser microsurgical apparatus 10. In this configuration, mirror 19 functions as a half mirror for the laser beams from source 21, but as a complete mirror for the laser beams from source 11. An operator can determine an optimum diameter size of the laser beams projected onto the cornea by observing the laser beams from source 21 through operation microscope 2.

Figure 4:
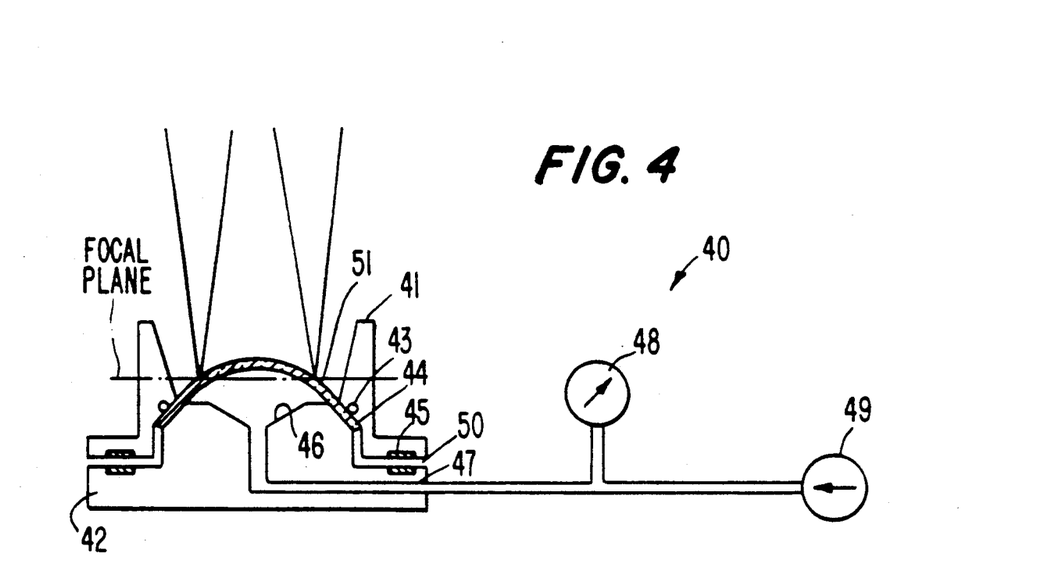
FIG. 4 illustrates a donor cornea holding device which may be used with the apparatus and method of the present invention.

For marking a donor corneal button, the noncontact laser microsurgical apparatus may be coupled to a donor cornea holding device 40 as shown in FIG. 4. Donor cornea holding device 40 is provided with a housing cover 41 and a receiving pedestal 42. Housing cover 41 includes an "O"-ring 43 disposed on an inner wall 44, and an annular magnet member 45. Receiving pedestal 42 includes a convex portion 46, a gas tube 47 extending from the center of the convex portion 46 to a pressure pump 49, a pressure gauge 48, and a magnet member 50 which is disposed opposite to and attracts the magnet member 45 of housing 41. In operation, a donor cornea or corneascleral tissue 51 is mounted on the receiving pedastal 42 and the housing cover 41 is placed over button 51. Due to attractive forces between magnet members 45 and 50, "O"-ring 43 presses the corneal button tightly to the housing pedestal 42. Pressurized gas or fluid is supplied to the underside of the corneal tissue 51 through the tube 47 so that the donor tissue is maintained with a constant underside pressure which may be controlled to correspond to the intraocular pressure of the live eye, about 15 mmHg-20 mmHg, by monitoring pressure gauge 48.

The steps of the method of the present invention for marking a cornea in transplanting surgery or keratoplasty can be carried out by using the noncontact laser microsurgical apparatus as hereinbelow described.

(1) A donor corneascleral tissue 51 cut out from a donor eye is mounted on the cornea holding device 40. The donor cornea is pressurized at normal intraocular pressure (15-20 mmHg) on the underside thereof by the fluid supplied from pump 49 through tube 47.

(2) The cornea holding device 40 is coupled to the laser microsurgical apparatus shown in FIG. 1 by appropriate mechanical means (not shown).

(3) Visible aiming laser light beams from source 21 are projected onto the cornea of a patient or onto a donor cornea through beam expander means 22, cold mirror 16, condensing lens 17, MFP axicon lens 18, and dichroic mirror 19.

(4) The visible aiming laser beams projected onto the cornea are observed through operation microscope 2. The diameter and position of the projected aiming laser beams are adjusted by moving the noncontact laser microsurgical apparatus and the operation microscope in tandem along optical axis $O_2$.

(5) Next, axicon lens 18 is moved along optical axis 01 so that the diameter or radial positions of paraxially distributed aiming laser beam spots from source 21 is adjusted to the desired size.

(6) After the diameter or radial positions of aiming laser beam spots has been set at an optimum size or radial position, control switch 11a is turned on and laser source 11 generates the infrared or ultraviolet pulsed laser beams.

Figure 5:
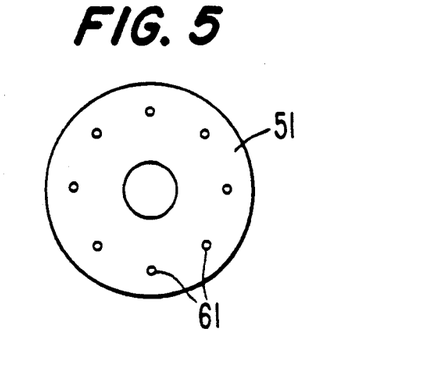
FIG. 5 is a plan view of a donor cornea marked by the apparatus of the present invention with spots defining a suture track.

(7) The pulsed laser beams are projected onto the cornea through the beam expander 13, cold mirror 16, condensing lens 17, MFP axicon lens 18 and the dichroic mirror 19, respectively, to mark the donor cornea or corneascleral tissue with spots 61 as shown in FIGS. 5 and 6. When irradiating laser energy is properly controlled, light-point marking in accordance with this particular embodiment of the method of the present invention can be carried out on the epithelium of the donor cornea 51.

(8) The donor cornea may then be trimmed or cut about its periphery so as to match the diameter of a recipient hole in the recipient cornea and is then preserved. A noncontact laser microsurgical cutting apparatus as disclosed in U.S. patent application Ser. No. 056,711, commonly assigned with this application and incorporated herein by reference, may be used to cut a donor corneal button and a recipient cornea.

Figure 7:
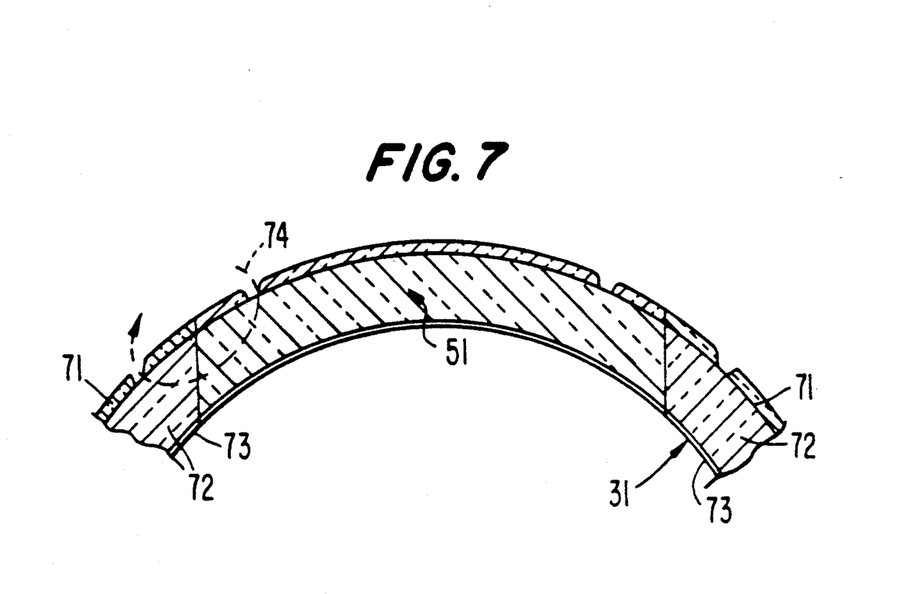
FIG. 7 is a cross-sectional view of the alignment shown in FIG. 6.

(9) After the cornea holding device 40 has been removed from the noncontact laser microsurgical apparatus, a recipient eye is set up as shown in FIG. 1. The recipient cornea is also subject to marking and cutting as stated in the above steps (3)-(8), provided, however, that the diameter and radial positions of the paraxially distributed beam spots 61 on the recipient cornea is made slightly larger than the diameter and radial positions of the beam spots 61 on the donor (10) Next, the donor corneal button 51 is aligned with the recipient cornea 52 by matching the paraxially distributed spots 61 as shown in FIG. 6. The cornea has epithelium 71, stroma 72, and endothelium 73 as shown in FIG. 7. The paraxially distributed spots 61 on the donor corneal button 51 and recipient cornea 31 may be marked only on the epithelium 71, or through the epithelium, the Bowman's layer and to a predetermined depth (for example 100 um) into the stroma, to create suture tracks.

(11) Suturing is then carried out through the paraxially distributed dots as indicated by dotted line 74 in FIG. 7.

By carrying out the steps of the first embodiment of the method of the present invention as described above, eight dots are marked on each of the donor corneal button 51 and the recipient cornea 31 as shown in FIG. 6.

When sixteen spots are required to be marked, after the first marking steps are carried out as described above, axicon lens 18 may be rotated by a predetermined angle about optical axis $O_1$, for example 22.5°, to mark an additional 8 spots. Similarly, an additional eight suture tracks are marked on the recipient cornea 31 so that sixteen symmetrical spots are marked on both the donor corneal button and the recipient cornea.

The noncontact laser microsurgical apparatus of the present invention may also be utilized in keratotomy, as will be described hereinbelow.

The diameter or radial positions of the distributed beam spots can be adjusted by moving MFP axicon lens 18 along optical axis $O_1$ as already explained hereinabove in connection with keratoplasty. Moreover, in radial keratotomy where the radial incisions or excisions made in the cornea extend outwardly from the apex of the cornea, the focal plane of the laser beams must be varied since the curvature of the cornea causes the radial incision or excisions in the cornea to be formed at varying distances from the laser source as the incision or excision moves progressively outward from the apex of the eye. Thus, to insure that the laser beams are brought to focus in the correct focal plane corresponding to the varying depths or distances at different radial positions on the cornea, the focal plane of the apparatus of the present invention is adjusted by moving condensing lens 17 along optical axis $O_1$.

Figure 8:
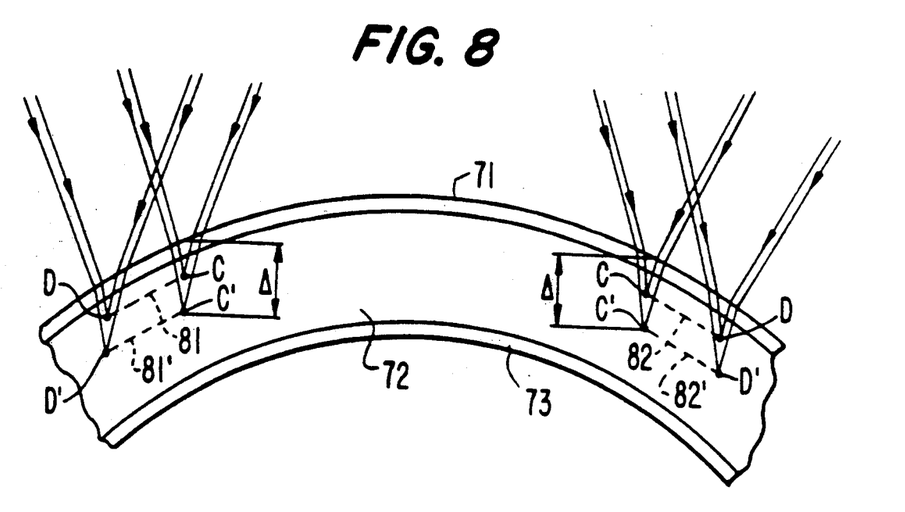
FIG. 8 is a cross-sectional view of a cornea of a patient's eye marked with incisions formed during radial keratotomy.
Figure 9:
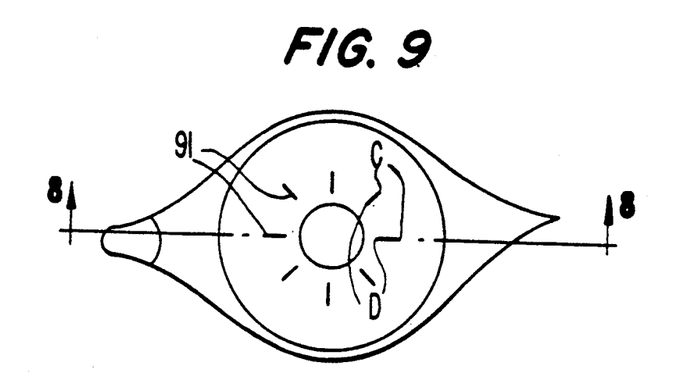
FIG. 9 illustrates a plan view of the eye shown in FIG. 8.

In radial keratotomy, wherein incisions or excisions are produced in the stroma and are oriented radially from the center of the cornea to the outer edge of the cornea, the curvature of a cornea is measured in advance by a keratometer so as to predict the distance of the focal plane of the laser beams at all radial positions on the cornea. With reference to FIG. 8, after the initial focal points "C" have been set in the upper portion of stroma 72, MFP axicon lens 18 is moved axially and preferably continuously within a predetermined range along optical axis $O_1$ so that radial incisions or excisions in stroma 72 may be made along the curvature of the cornea from points "C" toward points "D" as shown in FIGS. 8 and 9 FIG. 8 being a cutaway side view of FIG. 9 along lines 8—8. Simultaneously, condensing lens 17 is moved axially and preferably continuously along optical axis $O_1$ to adjust the focal plane of the laser beams to correspond to the radial position of the cornea at which the incision or excision is being made.

Laser energy from source 11 may be set to a sufficient energy to ablate and incise or excise the tissue of stroma 72 to a desired depth "Δ".

Figure 10:
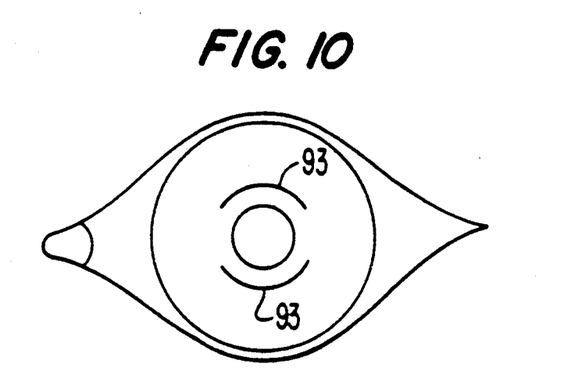
FIG. 10 illustrates a plan view of a patient's eye which has been subjected to curved keratotomy.

In curved keratotomy, wherein the excisions or incisions in stroma 72 are oriented as curved portions, i.e., as circumferential arcs spaced a predetermined and substantially constant radial distance from the apex or center of the cornea, MFP axicon lens 18 may be comprised of at least one two-facet prismatic lens. After focal points .C. have been set in stroma 72, MFP axicon lens 18 is rotated about optical axis $O_1$ within a predetermined rotating angle while laser source 11 is emitting beams of sufficient energy to ablate the stroma, thereby producing incisions or excisions in the stroma as illustrated in FIG. 10.

Figure 11:
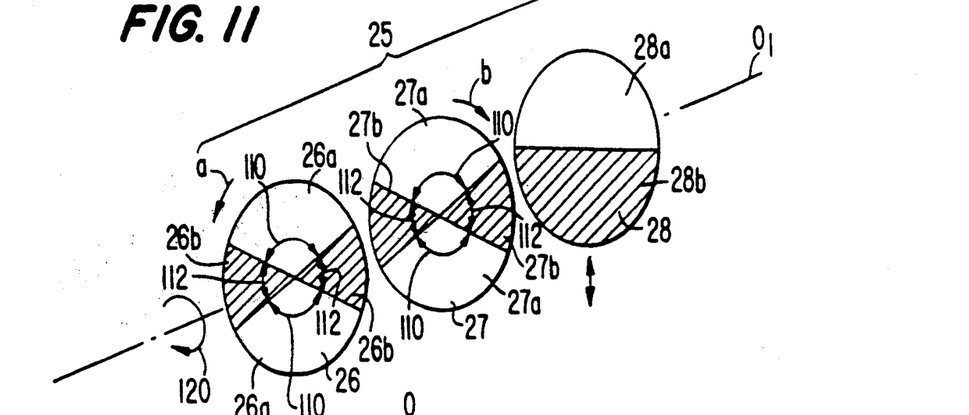
FIG. 11 illustrates one embodiment of a mask means which may be used with the present invention.

In another embodiment of curved keratotomy utilizing the apparatus and method of the present invention, MFP axicon lens 18 may be composed of at least one MFP lens having more than two facets, eight facets for example, which is rotatable about the optical axis $O_1$. Furthermore, apparatus 10 may include mask means, disposed between focusing and condensing lens 17 and cold mirror 16, for selectively defining at least one open aperture in optical axis $O_1$. In the present preferred embodiment, the mask means includes mask 25 having three mask units 26, 27, and 28 as shown in FIG. 11. Mask units 26 and 27 each include a pair of transparent portions 26a, 27a configured as 120° fan-shaped aperture angles 110 for transmitting laser beams emerging from cold mirror 16 therethrough, and a pair of opaque portions 26b, 27b configured as 60° fan-shaped aperture angles 112 for blocking the laser beams emerging from cold mirror 16.

Figure 12:
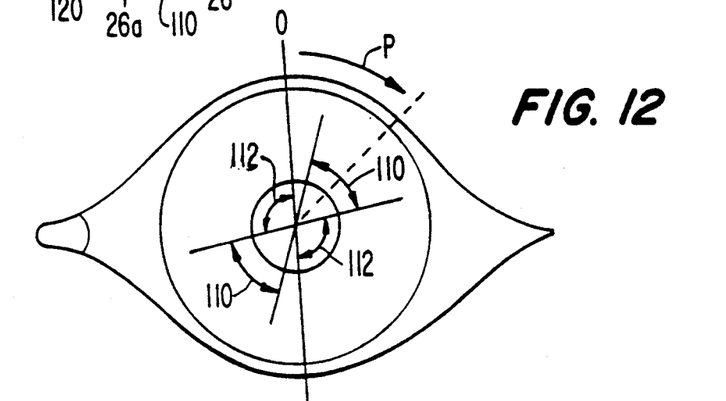
FIG. 12 illustrates the angular orientation of the apertures defined by the masked means of FIG. 11.

In accordance with the present invention, means may be provided for rotating mask units 26 and 27 in opposite directions, designated by arrows "a" and "b" in FIG. 11, relative one another about optical axis $O_1$ to change aperture angles 110a and 112a within a prescribed range, for example, between 60°-120° as illustrated in FIG. 12. As embodied herein the rotating means may comprise a stepping motor (not shown) controlled by a microprocessor (not shown). One skilled in the art will readily identify such motors and controllers, and, since the configuration of these motors and controllers do not themselves constitute any portion of the present invention, a detailed description is omitted. However, by way of example, a model no. SPH-35AB-006 type motor manufactured by Tokyo Electric Co., Ltd. may be used. Also, any suitable controller such as an IBM PC/AT may be used to control the motor.

The mask means may also include a mask unit 28 having a pair of semicircular portions 28a, 28b. Semicircular portion 28a is transparent to transmit laser beams therethrough, and semicircular portion 28b is opaque to the laser beams. Means may be provided to insert and remove mask unit 28 within optical axis $O_1$ to selectively block a portion of the laser beams from source 11, the blocked portion corresponding to the position of opaque semi-circular portion 28b. The mask units 26, 27 and 28 are constructed to be able to rotate in unison about optical axis $O_1$ to selectively position the apertures defined by masks 25 and 26 in optical axis $O_1$.

In this embodiment, after aperture angles 110a and 112a have been selected by individual opposite rotation of masks 25 and 26, and after the inclination angle β illustrated in FIG. 12 has been selected by common rotation about axis $O_1$ of masks 25 and 26 as a unit, the MFP axicon lens 18 rotates continuously in predetermined minute steps about optical axis $O_1$ for incising or excising the cornea.

The noncontact laser microsurgical apparatus and method of the present invention has further applications to thermokeratoplasty as will be described hereinbelow.

In thermokeratoplasty, for curing corneal refractive errors, e.g., hyperopia, myopia and/or astigmatism, laser source 11 may comprise an infra-red pulse type laser that emits a laser pulse having wavelengths of about 1.3 um to about 3.3 um. Laser source 11, in this embodiment, may comprise a Ho (Holmium) laser, for example, emitting at a wavelength of about 2.1 um.

Figure 13:
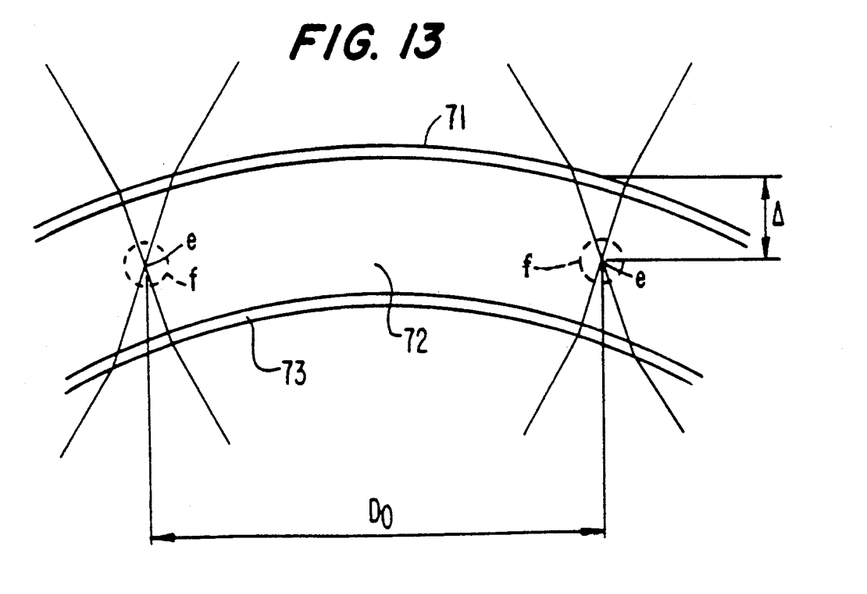
FIG. 13 illustrates a cutaway side view of a portion of the cornea wherein portions of the stroma of the cornea have been treated by thermokeratoplasty.

With reference to FIG. 13, in thermokeratoplasty for curing hyperopia, for example, after the focal points "C" have been set at points "e" with an optimum diameter and an optimum depth in the stroma 72 by independently moving focusing and condensing lens 17 and MFP axicon lens 18 along optical axis $O_1$ as has been described above, the Ho laser source 11 generates and projects the pulse laser beams onto the points "e".

Eight burns are formed instantly and simultaneously at the points "e" and cause shrinkage of the tissue of the stroma in the vicinity "f" around the points "e." The thermal effect of the laser causing shrinkage of the tissue about points "e" leads to a change of the shape of the cornea to alleviate hyperopia.

Figure 14:
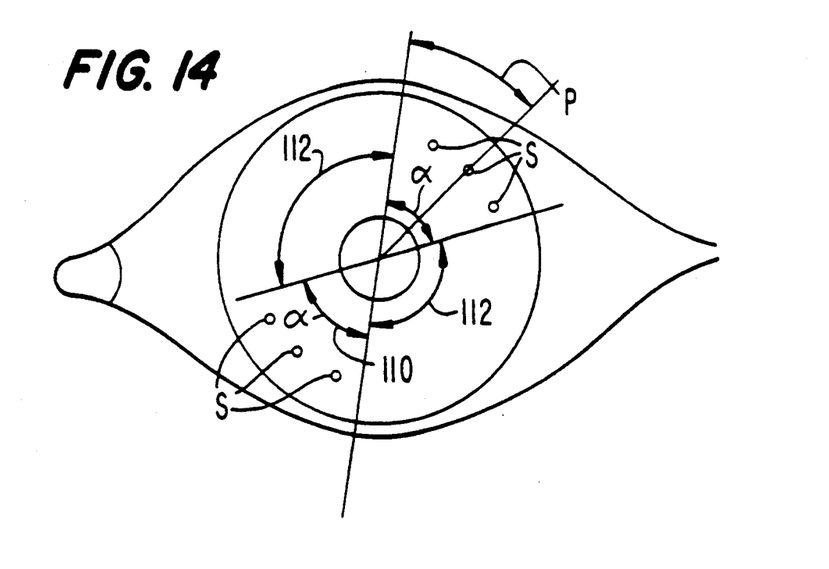
FIG. 14 illustrates a front view of an eye which has been treated in selected areas utilizing the method and apparatus of the present invention with mask means.

With reference to FIG. 14, in thermokeratoplasty for alleviating astigmatism, mask unit 25 may be used to selectively define the angular position b and the angle a, and to set the number of spots 61 projected onto the points "e". The thermal effect of the laser and the resulting shrinkage of tissue in vicinity "f" lead to a change of the shape of the cornea to alleviate the astigmatism.

In the embodiments of the method and apparatus of the present invention described above, the tissue of the cornea is impinged with laser beams of sufficient energy and for a sufficiently long time that the cornea is ablated by causing the fluids comprising the corneal tissue to go from solid or liquid phases to a gaseous phase. Such ablation is termed photo-vaporization when carried out using a hydrogen-fluoride short pulsed, and photodecomposition when carried out using an argon-fluoride excimer laser.

In other embodiments of the surgical method of the present invention, it is desirable not to vaporize or decompose the corneal tissue. Since the corneal tissue is comprised almost entirely of water, this means that under atmospheric pressure the temperature to which the corneal tissue is raised must be less than 100° C. This is best carried out with lasers having longer pulse durations, such as a long-pulsed C.W.HF laser, Nd:YAG laser, or a Holmium laser each having pulse durations greater than 200 ns and an energy flux of about 250 mJ/cm$^2$.

The inventors herein have discovered that above 60° C., the corneal tissue becomes adhesive and will begin to shrink. Thus, in one embodiment of the method of the present invention, selected areas of the cornea are impinged with laser beams having sufficient energy and for a sufficient time to heat the corneal tissue to less than about 100° C. to thereby cause shrinkage of the corneal tissue in those selected areas. In this manner the shape of the cornea and the curvature of the crystalline lens of the eye can be modified to alleviate astigmatism and/or corneal refractive error. Moreover, any of the embodiments of the apparatus of the present invention may be used in the practice of this method for shrinking corneal tissue to thereby control and define the selected areas of the cornea in which shrinkage is desirable.

In a further embodiment of the method of the present invention, where, during corneal transplant surgery, the donor cornea button has been placed in the recipient cornea, the abutting edges of the donor button and recipient cornea may be impinged with laser beams of sufficient energy and duration to heat the abutting edges to between about 60° C.-85° C. For this embodiment it is desirable to use a laser source having a pulse duration of greater than about 200 ns, a frequency of about 2.0-3.0 um, and an energy flux less than about 250 mJ/cm$^2$. In this manner, the tissue at the edges of the button and recipient hole become adhesive and attach to one another in a type of surgical weld thereby eliminating the need for sutures. This "welding" method may also be employed in epi-keratoplasty to attach a piece of cornea-like tissue over a whole recipient cornea to act in the manner of a contact lens. This cornea-like tissue may be human, animal or synthetic.

In a second embodiment of the present invention, a conical axicon lens 18' illustrated with the dot-dash line in FIG. 1 may used in place of MFP axicon lens 18. In such an embodiment the conical axicon lens need not be rotated about optical axis $O_1$ to perform curved keratotomy because the conical axicon lens converts the laser beams exiting from condensing and focusing lens 17 into annular beams and projects them toward the patient s cornea.

Figures 15, 16:
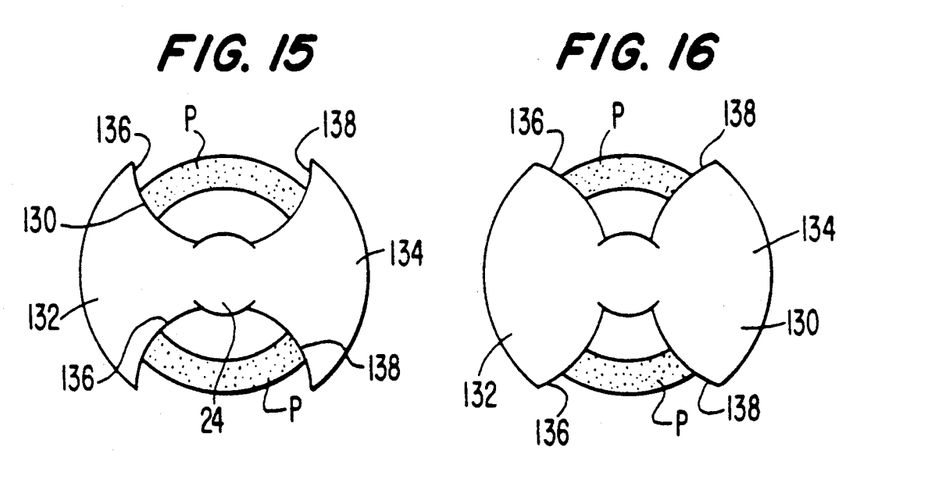
FIG. 15 illustrates another embodiment of the mask means of the present invention.
FIG. 16 illustrates still another embodiment of the mask means of the present invention.

Each of FIGS. 15 and 16 illustrate alternative embodiments of the mask means. In both alternative embodiments of the mask means, two masks are spaced from one another on optical axis $O_1$. Each mask is identical in configuration. Therefore, only one of the masks, mask 130, is illustrated in FIGS. 15 and 16.

Figure 17:
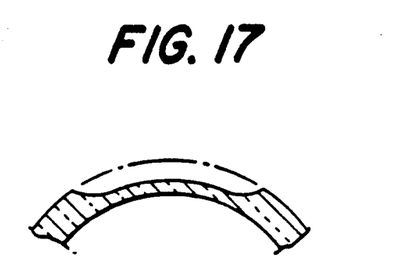
FIG. 17 is a cutaway side view of a portion of a cornea ablated by using the method and apparatus of the present invention and which illustrates the configuration of the cuts in the cornea which may be made utilizing the mask means of FIGS. 15 and 16.

By way of example and not limitation, mask 130 may comprise a metal plate having two fan-shaped opaque portions 132 and 134, and side edges 136 and 138 which are formed in a concave arc as shown in FIG. 15, or in a convex arc as shown in FIG. 16. Since the energy density of arc laser beams emerging through the aperture defined by side edges 136 and 138 decreases gradually along the radial direction of the arcs defined by the side edges 136 and 138, the depth of the incised or excised cut on the patient's cornea is shallowed gradually and smoothly at both end portions as shown in FIG. 17 such that delicate or subtle curved keratotomy may be carried out utilizing the method and apparatus of the present invention.

Figure 18:
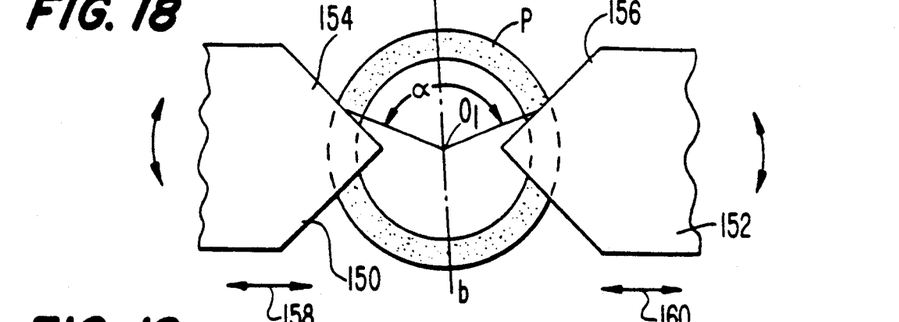
FIG. 18 illustrates still another embodiment of the mask means of the present invention.

FIG. 18 illustrates a still further embodiment of the mask means. Therein, masks 150 and 152 having wedge shaped portions 154 and 156, respectively, may be moved simultaneously or individually in opposite directions relative one another along arrows 158 and 160, respectively. In this manner, the aperture angle a defined by the edges of the wedge portions 154 and 156 may be selected in a predetermined manner. Furthermore, masks 150 and 152 may be rotated individually or in unison by any suitable motor or manual means about optical axis $O_1$ to selectively define the position angle b of the incised or excised cuts on the cornea of the eye.

Figure 19:
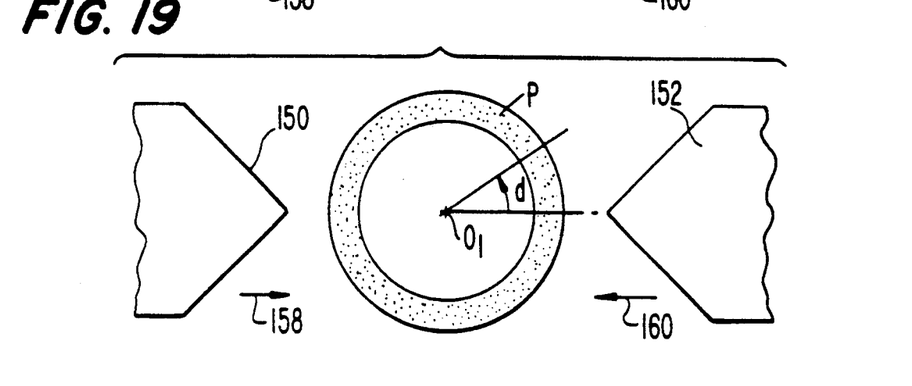
FIG. 19 illustrates the fully open position of the mask means of FIG. 18.
Figure 20:
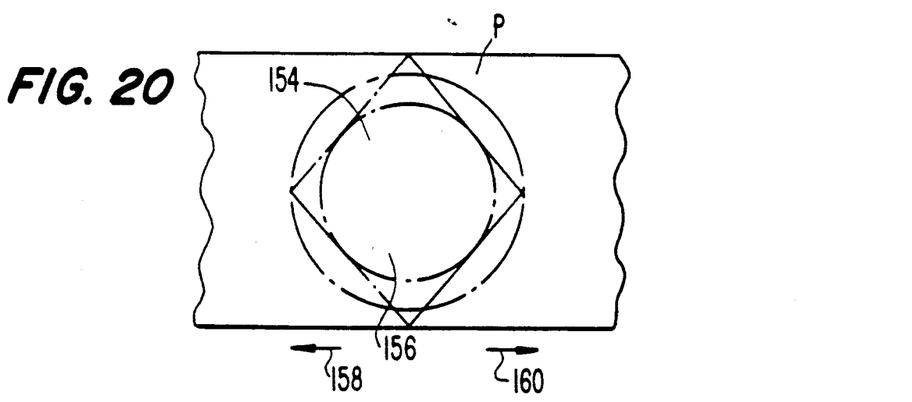
FIG. 20 illustrates the fully closed position of the mask means of FIG. 18.

Utilizing the mask means illustrated in FIG. 18, masks 150 and 152 may be moved towards each other along directions 158 and 160, respectively, during impingement of the cornea with laser beams. In FIG. 19, masks 150 and 152 are in the fully open state such that no portion of the cornea is blocked by wedge portions 154 and 156. As masks 150 and 152 are moved closer together as illustrated in FIG. 18, wedge portions 154 and 156 selectively block larger portions of the cornea from the laser beams emitted by source 11. In FIG. 20, wedge portions 154 and 156 overlap each other to fully block the cornea from any laser beams emitted by source 11.

Figure 21:
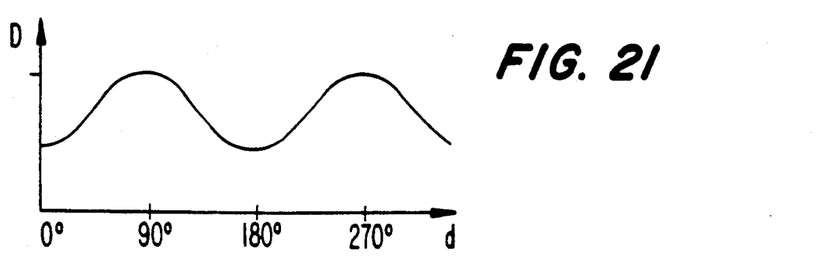
FIG. 21 illustrates the relationship between the incised or excised depth of cuts made in the stroma and the circumferential position of annularly shaped laser beams projected by the mask means of FIG. 18.

Utilizing the mask means illustrated in FIG. 18 in combination with a conical axicon lens, the annular laser beams P projected onto the cornea are changed in total emitted energy in accordance with the circumferential position d as illustrated in FIG. 19. Therefore, the incised or excised depth D of the cuts made in the stroma are gradually changed in depth to resemble a sine curve as illustrated in FIG. 21. In this manner, alleviation of corneal astigmatism may be carried out more delicately and subtly utilizing the teachings of the present invention to cure not only corneal astigmatism, but also corneal spherical power error.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. A noncontact laser microsurgical apparatus, comprising:
   means for generating laser beams;
   means for projecting said laser beams toward a cornea, said projecting means defining an optical axis, and including:
   means for converging the laser beams onto the cornea; and
   axicon means including an axicon lens having at least two prismatic facets for forming the converged laser beams into a plurality of paraxially distributed beam spots on the cornea; and
   means for rotating said axicon means relative to said optical axis of said projecting means.

2. A noncontact laser microsurgical apparatus as in claim 1, wherein said converging means includes condensing lens means for focusing said laser beams on the cornea.

3. A noncontact laser microsurgical apparatus as in claim 1, wherein said axicon lens consists of eight prismatic facets.

4. A noncontact laser microsurgical apparatus as in claim 1, wherein said pulsed laser beam generator comprises an ultra-violet laser beam source.

5. A noncontact laser microsurgical apparatus as i claim 1, including means for adjusting a radial position of said beam spots relative to an apex of the cornea.

6. A noncontact laser microsurgical apparatus as in claim 1, including means for moving said converging means along said optical axis of said projecting means.

7. A noncontact laser microsurgical apparatus as in claim 1, including mask means for selectively defining at least one light transmissive aperture and at least one opaque aperture in said optical axis of the projecting means, wherein said mask means includes at least two mask plates each having a wedge portion, and means for moving said wedge portions into and out of said optical axis of said projecting means to selectively block portions of said laser beams emitted by said generating means.

8. The noncontact laser microsurgical apparatus of claim 1, including mask means for selectively defining at least one light transmissive aperture and at least one opaque aperture in said optical axis of the projecting means, wherein said mask means includes at least two mask plates each having a wedge portion selectively movable into and out of said optical axis of said projecting means, and means for rotating at least one of said masks about said optical axis.

9. A noncontact laser microsurgical apparatus as in claim 1, wherein said projecting means includes beam expander means for enlarging a radius of said laser beams, and said converging means includes condensing lens means for focusing said laser beams on the cornea.

10. A noncontact laser microsurgical apparatus as in claim 9, wherein said beam expander means includes a variable diverging beam expander.

11. A noncontact laser microsurgical apparatus as in claim 1, including mask means for selectively blocking a portion of said laser beams, wherein said mask means includes at least two mask plates each having a wedge-shaped end portion, and means for moving said wedge-shaped portions of said mask plates into and out of said optical axis.

12. The apparatus of claim 11, including means for rotating at least one of said wedge-shaped portions about said optical axis.

13. A noncontact laser microsurgical apparatus as in claim 1, wherein said generating means includes an infrared pulsed laser beam generator.

14. A noncontact laser microsurgical apparatus as in claim 13, wherein said pulsed laser beam generator comprises an HF or an Er-YAG laser beam source.

15. A noncontact laser microsurgical apparatus as in claim 13, wherein the wavelength of beams generated by said infrared pulsed laser beam generator is within about 1.3 um to about 3.3 um.

16. A noncontact laser microsurgical apparatus as in claim 1, further including aiming means for projecting visible light beams onto the cornea at positions substantially coincident with positions to be impinged by said laser beams.

17. A noncontact laser microsurgical apparatus as in claim 16, wherein an optical axis of said aiming means overlaps a portion of the optical axis of said projecting means.

18. A noncontact laser microsurgical apparatus as in claim 16, wherein said aiming means includes a visible laser beam source, and mirror means, obliquely interposed between said generating means and said converging means, for reflecting the visible laser beams emitted by said aiming means and for transmitting the laser beams from said generating means therethrough.

* * * * *

UNITED STATES PATENT AND TRADEMARK OFFICE
CERTIFICATE OF CORRECTION

PATENT NO. : 5,281,211
DATED : January 25, 1994
INVENTOR(S) : Jean-Marie Parel et al.

It is certified that error appears in the above-indentified patent and that said Letters Patent is hereby corrected as shown below:

Claim 5, column 12, line 66, change "i" to --in--.

Signed and Sealed this

Fifteenth Day of November, 1994

Attest:

BRUCE LEHMAN

Attesting Officer        Commissioner of Patents and Trademarks